(12) United States Patent
Melbouci et al.

(10) Patent No.: US 6,562,090 B1
(45) Date of Patent: May 13, 2003

(54) FLUID ABRASIVE SUSPENSION FOR USE IN DENTIFRICES

(75) Inventors: Mohand Melbouci, Wilmington, DE (US); Jashawant J. Modi, Hockessin, DE (US)

(73) Assignee: Hercules Incorporated, Wilmington, DE (US)

( * ) Notice: Subject to any disclaimer, the term of this patent is extended or adjusted under 35 U.S.C. 154(b) by 0 days.

(21) Appl. No.: 09/649,626

(22) Filed: Aug. 28, 2000

(51) Int. Cl.[7] .............................. B24D 3/02; C09C 1/68; C09K 3/14; A61K 7/16
(52) U.S. Cl. .............................. 51/308; 51/307; 51/309; 424/49
(58) Field of Search ................. 51/302–309; 424/49–58

(56) References Cited

U.S. PATENT DOCUMENTS

| | | | | | |
|---|---|---|---|---|---|
| 3,506,757 A | * | 4/1970 | Salzmann | .................... | 464/52 |
| 3,839,213 A | * | 10/1974 | Hill | ............................ | 510/116 |
| 4,161,394 A | * | 7/1979 | Regan | ........................ | 51/302 |
| 4,254,101 A | | 3/1981 | Denny, Jr. | .................... | 424/52 |
| 4,314,990 A | | 2/1982 | Denny, Jr. et al. | ............. | 424/52 |
| 4,483,848 A | * | 11/1984 | Cox et al. | ..................... | 424/49 |
| 4,717,713 A | * | 1/1988 | Zatz et al. | ..................... | 514/2 |
| 4,842,763 A | * | 6/1989 | Truger et al. | ............... | 252/155 |
| 4,918,874 A | * | 4/1990 | Tiefenbach | .................... | 51/293 |
| 5,000,989 A | * | 3/1991 | Ford | ............................ | 427/387 |
| 5,156,672 A | * | 10/1992 | Bishop | ........................ | 406/1.05 |
| 5,156,835 A | | 10/1992 | Nabi et al. | ..................... | 424/52 |
| 5,266,088 A | * | 11/1993 | Sandusky et al. | ............. | 51/298 |
| 5,300,130 A | * | 4/1994 | Rostoker | ...................... | 51/309 |
| 5,310,543 A | * | 5/1994 | Dawson | ........................ | 424/40 |
| 5,368,843 A | * | 11/1994 | Ronnie | ......................... | 424/49 |
| 5,389,387 A | * | 2/1995 | Zuniga et al. | ................. | 426/74 |
| 5,455,050 A | * | 10/1995 | Beyerle et al. | ............. | 424/682 |
| 5,527,204 A | * | 6/1996 | Rhoades | ....................... | 451/40 |
| 5,631,026 A | * | 5/1997 | Beyerle et al. | ............. | 424/682 |
| 5,677,058 A | * | 10/1997 | Rhoades | ....................... | 451/40 |
| 5,716,600 A | * | 2/1998 | Zahradnik et al. | ............ | 424/52 |
| 5,741,471 A | * | 4/1998 | Deutsch et al. | ............. | 423/432 |
| 5,964,644 A | * | 10/1999 | Rhoades | ....................... | 451/40 |
| 6,037,380 A | * | 3/2000 | Venables et al. | ............. | 514/781 |
| 6,228,161 B1 | * | 5/2001 | Drummond | .................. | 106/464 |
| 6,254,905 B1 | * | 7/2001 | Hojo et al. | .................... | 426/74 |
| 6,288,154 B1 | * | 9/2001 | Rhoades | ....................... | 524/406 |
| 6,306,933 B1 | * | 10/2001 | Eiger et al. | ................. | 523/305 |
| 6,403,059 B1 | * | 6/2002 | Martin et al. | .................. | 424/49 |
| 6,419,174 B1 | * | 7/2002 | McGill et al. | ................. | 51/317 |

* cited by examiner

Primary Examiner—Shep K. Rose
(74) Attorney, Agent, or Firm—David Edwards

(57) ABSTRACT

A fluid abrasive suspension composition has an abrasive, suspending vehicle, and a water-swellable or water-soluble polymer. This composition is used to make a stable dentifrice formulation.

25 Claims, No Drawings

FLUID ABRASIVE SUSPENSION FOR USE IN DENTIFRICES

This invention relates; to a stable, fluid suspension of an abrasive material, a process for preparing such suspension, and the use thereof in dentifrices

BACKGROUND OF THE INVENTION

Prior to the present invention, it was difficult to suspend abrasive materials for use in the dentifrice industry and consequently the amount of abrasive material in wet compositions was inconsistent. The normal manner of using the abrasive was to suspend it in water and then mix it with the other components. In this manner, especially when high volumes of abrasive were used, the abrasive would some times settle out causing the amount of abrasive in the final composition to vary from batch to batch. Another option for getting the abrasive in the final dentifrice composition was to use a dry powder abrasive. Although this produced consistent compositions, dusting problems were often experienced resulting in a longer toothpaste production process. The longer preparation time is due to the fact that the abrasive, such as calcium carbonate, had to be added slowly over a certain period of time to minimize dusting as well as agglomeration of finely divided particles upon contact with the dentifrice gel premix. Dusting also created safety and health hazards by making the floor where the composition was being prepared slippery so that accidents could occur. Also, this dusting was a health problem for the workers who had to inhale this dust creating respiratory problems.

For the above reasons, plant operators desire a fast, effective, consistent, and simple way to incorporate abrasives into a dentifrice system. In other words, to reduce production costs as well as dusting in current toothpaste production, it is desirable to deliver a slurry or a fluid system (i.e., suspension or dispersion) of the abrasive. The use of such a slurry or fluid system will also allow manufacturers to use a continuous and/or batch production process that is efficient.

SUMMARY OF THE INVENTION

The present invention is directed to a fluid suspension consisting essentially of a) an abrasive, b) a suspending vehicle, and c) a water-swellable or water-soluble polymer.

The present invention also relates to a method of making a fluid suspension comprising dispersing and hydrating a polymer in a suspending vehicle of water or polyhydric alcohol or mixtures thereof and adding an abrasive to form the fluid suspension. Also, this system can be prepared in the reverse order by adding the abrasive to the suspending vehicle and then adding the polymer thereto. The fluid abrasive suspension can also be prepared by mixing in dry form a polymer and a abrasive to form a mixture and then adding a suspending vehicle of water, polyhydric alcohol, or mixtures thereof to said mixture and stirring to form the fluid suspension. Also, the fluid suspension can be prepared adding the ingredients in the reversed order, i.e., mixing the polymer and the abrasive, either together or alone, into the suspending vehicle.

The present invention also comprehends a method of making a dentifrice comprising adding to the above mentioned fluid abrasive suspension composition the desired dentifrice formulation ingredients. Again, the reverse order of addition can be used in that the desired dentifrice formulation ingredients can be added either alone or together to the fluid abrasive suspension mentioned above.

DETAILED DESCRIPTION OF THE INVENTION

It has been surprisingly found that abrasives could be made into stable fluid suspensions for a more efficient and consistent handling and use in the dentifrice industry. These suspensions have a long shelf life and thus can be shipped or pumped without the problems associated with settling. Another advantage of these fluid abrasive suspensions (FAS) is that since these FAS are made up of ingredients that are used in dentifrice, they are compatible and do not use ingredients that would be superfluous to dentifrice.

In accordance with this invention, the terms "suspension" and "dispersion" are used interchangeably to mean a system in which solid particles, the abrasive, are dispersed or suspended in a suspending vehicle of water or polyhydric alcohol or mixtures thereof to form a stable dispersion. Also, a "solution" is a homogeneous, single-phase mixture of a solvent such as water and a soluble material that is completely dissolved in the solvent. A "slurry" is defined as a liquid and an insoluble, solid material that forms a flowable mixture (such as mud or plaster of Paris).

A dentifrice is commercially available in four forms: powder, paste, gel, and liquid. The present invention is directed to all of the forms except powder. These forms are generally referred to as toothpaste. Hence, in this invention, the terms "dentifrice" and "toothpaste" will be used interchangeably.

The fluid abrasive suspension (FAS) of the present invention includes an abrasive, a suspending vehicle, and a water-swellable or water-soluble polymer. The FAS may also contain at least one other ingredient that may be used in dentifrices such as perservatives, fluoride, buffering agent, humectant, coloring agent, flavor, sudsing agent, detergent, salts, tartar control, sweetener, vitamin, whitening agent, antiplaque agent, anticalculus, sequestering agent, and odor removers.

Unless otherwise mentioned, all of the amounts in the FAS are based on the total weight of the FAS.

Abrasives

In accordance with the present invention, the FAS contains a lower limit of the abrasive of 5 weight percent on the total weight of the FAS, preferably 15 weight percent, and more preferably 30 weight percent. The upper limit in the FAS is 70 weight percent, preferably 60 weight percent, and more preferably 45-weight percent. In toothpaste, abrasives of various types can provide the unique benefits of exceptional dental cleaning and polishing performance without unduly abrading tooth enamel or dentin. The abrasive materials must also be exceptionally compatible with sources of soluble fluorides. Hence, it is important that the correct amount of abrasive be in the toothpaste so that it can perform its intended purpose well.

In accordance with this invention, the bulk density of the abrasive polishing material should be in a specific range. If the bulk density is too low, it becomes more difficult to incorporate the abrasive into the suspension system. If the bulk density is too high, it becomes impractical to handle and use. Hence, there is a desirable range that should be used. This makes it easy for processing and pumping the abrasive from one stage to the next in the making of a dentifrice formulation. The lower limit of the bulk density is about 0.2 gram per milliliter (g/ml), preferably 0.4 g/ml, and more preferably 0.6 g/ml. The upper limit of the bulk density is about 1.2 g/ml, preferably 1.0 g/ml, and more preferably 0.8 g/ml.

Examples of abrasive materials that can be used in this invention are calcium carbonate, calcium phosphate, sodium meta phosphate, sodium bicarbonate, calcium pyrophosphate, dicalcium phosphate, silica, and alumina. The preferred abrasives are calcium carbonate, especially precipitated calcium carbonate (PCC), dicalcium phosphate (Dical), and silica.

Suspending Vehicle

In accordance with the present invention, the suspending vehicle of the FAS can be water, a polyhydric alcohol, or mixtures thereof. Water used in this invention should preferably be deionized or demineralized and free of organic impurities. When water is used alone in the FAS, it should have a lower limit amount of 25% by weight of the FAS formulation, preferably 35% and more preferably 45%. The upper limit for the water should be 90%, preferably 75% and more preferably 60%.

Some examples of the polyhydric alcohols which can be used with water are: sorbitol, glycerol, propylene glycol, polyethylene glycol, ribitol, xylitol, mannitol, poloxamer, and mixtures thereof.

The anhydrous polyhydric alcohols (PHALC) which can be used alone for FAS without presence of water are: propylene glycol (PG), polyethylene glycol (PEG), glycerol (G), and poloxamer (PXMR). For example, PG and PEG can be used with Klucel® polysaccharide and G can be used with Natrosol® product. These PHALC could also be used in combination with the other polyhydric alcohol mentioned above such as xylito, manitol, etc.

When the polyhydric alcohol is used alone in the FAS formulation, it should have a lower limit of about 25 wt %, preferably 30 weight percent, and more preferably 45 wt %. The upper limit amount can be about 90-wt. % preferably 75 wt % and more preferably 60 wt %.

In the present invention, when water and polyhydric alcohol are used in combination in the FAS, the amount of the combination should be about at least 25 wt %. The upper limit should be about 90 wt %, preferably 75 wt %, and more preferably 60 wt %. Preferred mixtures are water with sorbitol or glycerol with sorbitol or water, sorbitol and glycerol.

Water-Swellable or Water-Soluble Polymer

The polymer is the ingredient that provides stability to the FAS. Examples of the polymers that can be used in this invention are polysaccharides such as carrageenan, pectin, carboxymethylcellulose (CMC), hydroxyethylcellulose (HEC), hydroxypropylcellulose (HPC), ethylhydroxyethylcellulose (EHEC), methylcellulose (MC), hydroxypropylmethylcellulose (HPMC), xanthan gum, inorganic gelling or thickening agents such as clays (i.e., magnesium aluminum silicate), silica, silica precipitate, silica aerogel, pyrogenic silica, homo- or copolymer of acrylic acid or acrylic acid salt, polyvinylpyrolidene, gelatin, and mixtures thereof. The amount of tea polymer in the FAS can have a lower limit of about 0.1 wt % based on weight of the FAS, preferably 0.5 wt %, and more preferably 1.0 wt %. The upper limit amount is about 10 wt %, preferably 7.0 wt % and more preferably 3.0 wt %.

Toothpaste

In accordance with the present invention, toothpaste compositions contain an abrasive, a humectant, a fluoride ion source, a buffering agent, a detergent, and water. The humectant serves to keep the toothpaste composition from hardening upon exposure to air and provides freeze-thaw stability. Certain humectants can also impart desirable sweetness or flavor to toothpaste compositions. The humectants, on a pure humectant basis, generally comprise from about 5 wt % to about 80 wt %, preferably from about 20 wt % to about 35 wt % of the total toothpaste composition. Examples of humectants are the suspending vehicle, mentioned above.

The fluoride ions combine with dental enamel and thereby reduce enamel solubility in acid. The applying of fluoride ion to dental enamel protects teeth against tooth decay. The fluoride ion has to be present in the amount of from about 0.01 wt % to about 3.0 wt %, preferably from about 0.03 wt % to about 1.0 wt % of the toothpaste composition.

A buffering agent is used to adjust and maintain the toothpaste composition at the desired pH, which is generally in the range of 3.0 to 11.0, preferably 6.0 to about 9.0. Examples of buffering agents are phosphates and tris (hydroxymethyl)-aminomethane with water-soluble phosphate salts being preferred.

Detergents are used to produce suds in order to remove stains and foreign particles from the teeth and gums. Generally, detergents can be used in the toothpaste from about 0.2 wt % to about 3.0 wt %, preferably from about 0.75 wt % to about 1.5 wt %. Examples of detergents are sodium lauryl sulfate and sodium lauryl sarcosinate.

In addition to the above mentioned preferred ingredients, the toothpaste composition may optionally contain binding agents, sudsing agents, flavoring agents, sweetening agents, anticalculus agents, film formers, antiplaque agents, coloring agents, whitening agents, odor remover agents, breath fresher, vitamins, sequestering agents, salts, tartar control agents, pain killers, preservatives, and pigments.

Method of Making Toothpaste

Toothpaste of the present invention is prepared by mixing together in any order or by any conventional means the preferred and optional components herein.

In accordance with the present invention, a method of making a dentifrice comprising mixing a thickening agent, water, and a polyhydric alcohol to form a solution and adding to this solution the above mentioned fluid abrasive suspension composition. Also, any of the optional ingredients can be added as desired by the manufacturer. The normal pH range of toothpaste is about 3.0 to about 11.0, preferably 6.0 to 9.0. Other methods of making toothpaste are to add all of the ingredients individually or pre-blended as desired to the FAS or add the FAS to the preferred and optional ingredients in any order of addition.

The following examples are set forth merely to illustrate the present invention but are not intended to be limitations on the invention. All parts and percentages are by weight unless noted otherwise. The examples illustrate the preparation of FAS of abrasives such as: two types of calcium carbonates (PCC1 and PCC2); dicalcium phosphate (Dical); silica; dical/sodium bicarbonate; and dical/silica.

PROCEDURE 1

Standard Method for Making FAS Formulations in Tables 1–6

1. Sorbo® product, glycerin, Carbowax® product, and water were added to a Griffin beaker and agitated with a "Jiffy"

mixture agitator and Caframo stirrer until the mixture became homogeneous. A preservative and then salts were added to the formulations where mentioned and mixed until the mixture became homogeneous again.

2. A water-soluble or water-swellable polymer(s) was slowly sifted into the solution to avoid lumping and was mixed until smooth with no lumps (~1 hr).
3. An abrasive(s) was then carefully added to the mixture to avoid dusting and the dispersion was allowed to mix for an additional 60 minutes to make a homogenous FAS. The sides of the vessel were scraped occasionally during the mixing step to ensure uniformity.
4. The FAS was then transfer to 4 oz. sample jars and allowed to rest at room temperature.
5. All samples were prepared with 60-wt % abrasive unless noted otherwise.

pH and Viscosity Measurement

1. Prior to making the measurements at each time interval, the samples were placed in a water bath at a temperature of 25° C. for at least 4 hours. The samples were observed and measured at 1 day, 2 days, and 7 days.

TABLE 1

Suspensions of Precipitated CaCO$_3$ (PCC)

| Example No. Ingredients (g) | 1 | 2 | 3 | 4 | 5 |
|---|---|---|---|---|---|
| Sorbo ® (70%)[a] | 50.00 | 50.00 | 50.00 | 98.50 | — |
| D H$_2$O[b] | 48.00 | 48.25 | 48.50 | — | 95.625 |
| CMC 7MXF[c] | 0.75 | 0.50 | 0.25 | 0.25 | 3.125 |
| Suttocide A[d] | 1.25 | 1.25 | 1.25 | 1.25 | 1.25 |
| PCC1[e] | 150.00 | 150.00 | 150.00 | 150.00 | 150.00 |

[a]Sorbo ® product is a trademark of ICI Company and is used to market 70 wt % Sorbitol in water.
[b]DH$_2$O means deionized water free of organic impurities.
[c]CMC 7MXF means carboxymethyl cellulose having a DS of 0.65 to 0.9 & water viscosity of 400–800 cps at 25° C., marketed by Hercules Incorporated
[d]Suttocide A is a preservative marketed by ISP Co. of Chatham, NJ.
[e]PCC1 is precipitated CaCO$_3$ having a bulk density of about 0.834 g/ml.

TABLE 2

Properties PCC Suspensions

| Example | Days Stored | Condition | pH | *Viscosity (cP) At rest/after mixing | Comments/Observations |
|---|---|---|---|---|---|
| 1 | 1 | RT | 9.28 | 1300/780 | Some settling, watery surface, pourable, remixable. |
|   | 2 | RT | 9.32 | 1033/650 | Same as 1 day w/more settling, very sludgy bottom. |
|   | 7 | RT | 9.23 | 1575/683 | Same as 1 day w/more settling, very sludgy bottom. |
| 2 | 1 | RT | 9.26 | 2066/566 | Some settling, watery surface, sludgy bottom, pourable, mixable. |
|   | 2 | RT | 9.34 | 408/367 | Same-as 1 day. |
|   | 7 | RT | 9.34 | 6450/350 | Watery surface, very sludgy bottom, mixable. |
| 3 | 1 | RT | 9.32 | 2958/50 | Some settling, watery surface, sludgy bottom, pourable, remixable. |
|   | 2 | RT | 9.28 | —/— | Same as 1 day. |
|   | 7 | RT | 9.40 | 20,425/75 | Watery surface, sludgy bottom, remixable. |
| 4 | 1 | RT | 9.22 | 16,920/17,480 | No settling, uniform, pourable, remixable, less viscous than ~5. |
|   | 2 | RT | 9.26 | 16,550/12,580 | Same as 1 day. |
|   | 7 | RT | 9.05 | 17,217/15,133 | Slight settling, otherwise same. |
| 5 | 1 | RT | 9.44 | 25,215/13,230 | No settling, uniform, pourable, remixable, most viscous. |
|   | 2 | RT | 9.46 | 28,680/12,660 | Same as 1 day. |
|   | 7 | RT | 9.58 | 28,680/12,566 | Same as 1 day. |

*Brookfield RVT Helipath @ 20 RPM and 25° C.

2. The samples were first visually observed by the lab personnel for settling and syneresis (based on percent by volume).
3. Without disturbing the sample, the viscosity was measured for each sample using a Brookfield RVT viscometer with the Helipath set at 20 RPM. Over a 3-minute period, 6 measurements were made at 30-second time intervals. This is the "at rest" measurement.
4. The pH was then measured and recorded.
5. Next the samples were re-mixed for exactly 3 minutes using a Caframo mixer and small "jiffy" type agitator with the Caframo mixer set at 1200 RPM. The agitator was close to the bottom of the sample jar so that any settled material was resuspended.
6. The average viscosity was re-measured using the same procedure as above. This is the "After Mixing Measurement."

Examples 1 through 3 looked at the effect of CMC 7MXF concentration on PCC1 suspending ability in a 50/50 mixture of water and Sorbo product (70% Sorbitol). Settling is observed in all Examples at 1 day and becomes progressively worse with time. As expected, settling occurred more rapidly at the lower CMC concentrations with the formation of a soft pellet at the bottom. However, all Examples remained readily remixable and the settled abrasive could be resuspended.

Example 4 evaluated the suspending ability of CMC 7MXF in a lean solvent system (70% Sorbitol). At 0.25 g (0.1 wt %) polymer, a stable suspension of PCC1 was obtained and the viscosity was ~17,000 cps @ 2 days.

Example 5 evaluated the suspending ability of CMC 7MXF in an aqueous system. The CMC level was increased in this Example to 3.25 g (1.25 wt %) concentration. At this CMC level a stable suspension was obtained and the viscosity was ~29,000 cps @ 2 days.

TABLE 3

PCC Suspensions

| Example No. | 6 | 7 | 8 | 9 | 10 | 11 |
|---|---|---|---|---|---|---|
| Sorbo (70%) | 50.00 | 25.00 | 98.75 | — | — | 50.00 |
| Glycerin[a] | — | 25.00 | — | — | — | — |
| Carbowax 200[b] | — | — | — | — | 24.375 | — |
| DH$_2$O | 47.50 | 48.00 | — | 96.50 | 73.125 | 47.60 |
| CMC 7MXF | 1.25 | 0.75 | — | 2.25 | 1.25 | 1.25 |
| Suttocide A | 1.25 | 1.25 | 1.25 | 1.25 | 1.25 | 1.25 |
| Dical[c] | — | — | — | — | — | 150.00 |
| PCC1 | 150.00 | 150.00 | 150.00 | 150.00 | 150.00 | — |

[a]Glycerin is a USP grade, marketed by Textile Chemical Co. of Readig PA.
[b]Carbowax ®200 is a trademark covering polyethylene glycol, marketed by Union Carbide Co., USA.
[c]Dical means declaim phosphate dehydrate, grade 251, marketed by Solutia, Inc of St Louis Mo.

Example 8 was the control for Example 4. No polymer addition was made and Sorbo product was the oily vehicle. Settling was observed within one day and a soft pellet was formed in the bottom of the Example. The viscosity was about 18,000 cP at 2 days.

Example 9 evaluated CMC 7MXF in a 100% aqueous system again, this time at a level of 0.50 wt %. A stable suspension was obtained at this concentration and the viscosity was ~7500 cps @ 2 days.

Example 10 evaluated CMC 7MXF at 0.50 wt % in a 25/75 mixture of Carbowax® 200 product and water. A stable suspension was obtained at this concentration and the viscosity was ~5000 cps @ 2 days.

Example 11 evaluated CMC 7MXF at 0.50 wt % in a 50/50 mixture of Sorbo product and water. Dicalcium phosphate dihydrate was substituted for calcium carbonate as the abrasive in this Example. A uniform suspension was obtained at this concentration and the viscosity was ~18,000 cps @ 2 days. Note that the viscosity for the calcium

TABLE 4

Properties of PCC Suspensions

| Example No. | Days Stored | Condition | pH | Viscosity (cps) At rest/after mixing | Comments/Observations |
|---|---|---|---|---|---|
| 6 | 1 | RT | 9.31 | 10,050/5400 | Pourable, uniform, no settling. |
|   | 2 | RT | 9.34 | 9650/5100 | Same as 1 day. |
|   | 7 | RT | 9.27 | 9033/5283 | Same as 1 day. |
| 7 | 1 | RT | 9.18 | 2008/1750 | Pourable, uniform, no settling. Easier to mixture |
|   | 2 | RT | 9.26 | 2892/1717 | Same as 1 day. |
|   | 7 | RT | 9.33 | 2166/1583 | Slight settling, otherwise same. |
| 8 (control) | 1 | RT | 9.00 | 18,220/14,300 | Settling, sludgy on bottom, pourable. |
|   | 2 | RT | 9.04 | 18,080/14,750 | Same as 1 day. |
|   | 7 | RT | 8.90 | 18,420/12,216 | Same as 1 day. |
| 9 | 1 | RT | 9.28 | 7942/3783 | Pourable, uniform, no settling. |
|   | 2 | RT | 9.30 | 7525/3908 | Same as 1 day. |
|   | 7 | RT | 9.29 | 7633/3792 | Same as 1 day. |
| 10 | 1 | RT | 9.06 | 5225/2017 | Pourable, uniform, no settling. |
|   | 2 | RT | 9.08 | 4708/2383 | Same as 1 day. |
|   | 7 | RT | 9.14 | 4942/2575 | Same as 1 day. |
| 11 | 1 | RT | 7.19 | 17,216/9408 | Pourable, uniform, no settling. |
|   | 2 | RT | 7.21 | 18,300/10,250 | Same as 1 day. |
|   | 7 | RT | 7.68 | 34,280/10,680 | Same as 1 day. |

Example 6 evaluated CMC 7MXF again in a 50/50 mixture of Sorbo® product and water at a concentration of 0.50 wt %. A stable suspension was obtained at this concentration with the viscosity ~10,000 cps @ 2 days.

Example 7 evaluated CMC 7MXF at 0.50 wt % again, but in a 25/25/50 mixture of Sorbo product, glycerin, and water. The resulting suspension was stable with only slight settling at 7 days. The viscosity of the Example was about 2000 cP.

carbonate slurry is lower than that of the dical slurry in the same system (Example 6 vs. Example 11).

In summary, a stable suspension of PCC1 was obtained in presence of CMC. We could not make a stable PCC1 suspension without the addition of CMC. At the lower CMC concentrations where settling occurred, the pellet formed was softer and easier to remix than in the Example with no CMC addition.

TABLE 5

PCC1 Suspensions

| | Example No | | | | | | | |
|---|---|---|---|---|---|---|---|---|
| | 12 | 13 | 14 | 15 | 16 | 17 | 18 | 19 |
| Sorbo ® | | | — | | | 20.00 | 20.00 | 20.00 |
| Glycerin | — | | | | | | | |
| Carbowax ® 200 | | — | | | | | | |
| Propylene glycol[a] | | | | | | | | |
| Ethanol | | | | | | | | |
| DH$_2$O | 79.50 | 78.50 | 39.50 | 19.50 | 29.20 | 19.50 | 19.00 | 19.20 |
| Suttocide ® A | 0.50 | 0.50 | 0.50 | 0.50 | 0.50 | 0.00 | 0.50 | 0.50 |

TABLE 5-continued

PCC1 Suspensions

| | Example No | | | | | | | |
|---|---|---|---|---|---|---|---|---|
| | 12 | 13 | 14 | 15 | 16 | 17 | 18 | 19 |
| CMC 7MXF | — | 0.75 | | | | 0.50 | 0.5* | |
| Xapthan Gum[b] | | 0.25 | | | 0.30 | | | |
| Carbopol ® 980** | | | | | | | | |
| Klucel ® GF NF[c] | | | | | | | | |
| GENUVISCO TPC1[d] | | | | | | | | 0.30 |
| Sylodent ® 15[e] | | | | | | | | |
| SMFP[f] | | | | | | | | |
| PCC1 | 20.00 Control | 20.00 | 60.00 Control | 80.00 Control | 70.00 | 60.00 | 60.0* | 60.00 |

[a]This is a USP grade, marketed by EM Science Co., Gibbstown, NJ.
[b]This is Kelco K 6B166 grade, marketed by Kelco Co. of San Diego, CA.
[c]This is hydroxypropylcellulose (HPC) with Brookfield viscosity of 150 to 400 cps at 2% and 25° C., marketed by Hercules Incorporated.
[d]This trademark covering carrageenan, marketed by Hercules Incorporated.
[e]This is a trademark covering synthetic amorphous silica, marketed by WR Grace Co., Baltimore, MD.
[f]This means sodium monoflouro phosphate, marketed by Johnson Mathey of Wardhill, MA.
*dry-blend prior to adding to the solvent system
**Carbopol 980 is a trademark covering carbomer, marketed by B. F Goodrich Co. of Cleveland, OH.

TABLE 6

PCC Suspensions

| Example | Days Stored | Condition | PH | *Viscosity(cP) At rest/after mixing | Comments/Observations |
|---|---|---|---|---|---|
| 12 (control) | 1 | RT | — | —/— | PCC settled, clear supernatant. 20/80. |
| | 2 | RT | — | —/— | PCC settled, clear supernatant. 20/80. |
| | 7 | RT | — | —/— | PCC settled, clear supernatant. 20/80. |
| 13 | 1 | RT | 9.47 | 658/875 | Uniform, no settling, low viscosity. |
| | 2 | RT | 9.44 | 592/600 | Very slight settling. |
| | 7 | RT | — | —/— | PCC settled, hazy supernatant. 33/67. |
| 11 (control) | 1 | RT | — | —/— | PCC settled, clear supernatant. 80/20. |
| | 2 | RT | — | —/— | PCC settled, clear supernatant. 80/20. |
| | 7 | RT | — | —/— | PCC settled, clear supernatant. 80/20. |
| 15 (control) | 1 | RT | — | —/— | Dry, crumby material. |
| | 2 | RT | — | —/— | Dry, crumby material. |
| | 7 | RT | — | —/— | Dry, crumby material. |
| 16 | 1 | RT | 9.20 | 22,750/7708 | Some settling, sludgy bottom, watery surface. |
| | 2 | RT | 9.21 | 24,030/6600 | ~4% syneresis**, clear supernatant, settling, sludgy bottom. |
| | 7 | RT | 9.20 | 28,320/6280 | ~4% syneresis**, clear supernatant, settling, sludgy bottom. |
| 17 | 1 | RT | 8.11 | 3425/2608 | Uniform, no settling. |
| | 2 | RT | 8.14 | 3608/2708 | Uniform, no settling. |
| | 7 | RT | 8.10 | 3880/2750 | Uniform, no settling. |
| 18 | 1 | RT | 9.35 | 7292/4250 | Uniform, no settling. |
| | 2 | RT | 9.43 | 6792/4317 | Uniform, no settling. |
| | 7 | RT | 9.46 | 6600/4520 | Uniform, no settling. |
| 19 | 1 | RT | 9.21 | 15,133/7742 | Uniform, no settling, gel like structure. |
| | 2 | RT | 9.42 | 12,833/7375 | Uniform, no settling, gel like structure. |
| | 7 | RT | 9.41 | 11,780/7160 | Uniform, no settling, gel like structure. |

*Brookfield RVT Helipath @ 20 RPM & 25° C.
**Syneresis is measured by volume.

Example 12 (control) evaluated the PCC1 at 20-wt % in a polymer free 100% aqueous system. As expected, settling of the abrasive occurred immediately.

Example 13 evaluated the PCC 1 at 20-wt % in 100% aqueous system containing 0.75 wt % CMC 7MXF and 0.25 wt % Xanthan gum. The resulting suspension showed only slight settling at 2 days and the viscosity of the suspension was about 600 cP at 2 days.

Example 14 (control) evaluated the PCC1 at 60-wt % in a polymer free 100% aqueous system. Again, settling of the abrasive occurred immediately.

Example 15 (control) evaluated the PCC1 at 80-wt % in a polymer free 100% aqueous system. The solids loading were too high for this system and a dry, crumby material was the result.

Example 16 evaluated the PCC1 at 70-wt % in a 100% aqueous system containing 0.30 wt % Xanthan gum. Settling was observed in this system at 1 day and the viscosity was about 24,000 cP at 2 days.

Example 17 evaluated the PCC 1 at 60-wt % in a 50/50 mixture of water and Sorbo with 0.50 wt % CMC 7MXF. The resulting suspension was uniform with no settling observed. The viscosity of the system was about 3500 cP at 2 days. The sample was prepared without the preservative.

Example 18 evaluated the same system as Example 17 except that the polymer dry-blended with the abrasive. Again, a uniform suspension was obtained. The viscosity of the Example 18 was about 6800 cP at 2 days.

Example 19 evaluated the PCC1 at 60-wt % in a 50/50 mixture of Sorbo® and water with 0.30 wt % GENU-VISCO® TPC-1 carrageenan. The resulting suspension was uniform with a gel-like structure. The viscosity of this system was about 13,000 cP at 2 days. This system was stable after 6 month's storage at room temperature.

In summary, the addition of polymer improved the stability of abrasive suspensions up to 70-wt % PCC1. Suspension Example 19 with GENUVISCO®0 TPC-1 carrageenan was the most stable of this series.

PROCEDURE 2

Standard Method for Making a 500 g Batch of Formulations in Tables 7–13

1. Sorbo® (70% sorbitol) product, glycerin, Carbowax® product, and water were added to a Waring blender and agitate until the mixture became homogenous. A preservative and then salts were added to the formulations where mentioned and mixed until the mixture became homogeneous again.
2. A water-soluble polymer(s) was slowly sifted into the vortex of the solution in the blender to avoid lumping and mixed until smooth with no lumps. (~10–15 mins.).
3. An abrasive(s) was then carefully added to the mixture to avoid dusting and the dispersion was allow to mix an additional 10–15 minutes to make a homogeneous FAS. The blender was turned off and the sides of vessel were scraped down occasionally to ensure uniformity of the mixture.
4. The FAS was then transferred to 4 oz. sample jars and allowed to rest at room temperature.
5. All Examples were prepared with 60-wt. % abrasive unless noted otherwise.

pH and Viscosity Measurement

1. Prior to making the measurements at each time interval, the samples were placed in water bath at a temperature of 25° C. for at least 4 hours. The samples were observed and measured at 1 day, 2 days, and 7 days.
2. The samples were first visually observed for settling and syneresis.
3. Without disturbing the sample, the viscosity was measured for each sample using a Brookfield RVT viscometer with the Helipath se at 20 RPM. Over a 3-minute period, 6 measurements were made at 30-second time intervals and averages of the 6 measurements were recorded. This is the "at rest" measurement.
4. The pH was then measured and recorded.
5. Next the samples were re-mixed for exactly 3 minutes using a Caframo mixer and small "Jiffy" type agitator with the Caframo mixer set at 1200 RPM. The agitator was kept close to the bottom of the sample jar so that any settled material was resuspended.
6. The average viscosity was re-measured using the same procedures above. This is the "after mixing" measurement.

TABLE 7

| | Example No. | | | | | | | | | | | | | |
|---|---|---|---|---|---|---|---|---|---|---|---|---|---|---|
| | 20 | 21 | 22 | 23 | 24 | 25 | 26 | 27 | 28 | 29 | 30 | 31 | 32 | 33 |
| Sorbo (70%) | 19.25 | 9.63 | 10.00 | | 10.00 | | | 10.00 | | 10.00 | | 10.00 | 20.00 | |
| Glycerin | | 9.62 | 10.00 | | 10.00 | | | 10.00 | | 10.00 | | 10.00 | | |
| Carbowax 200 | | | | | | | | | | | | | | |
| Propylene glycol | | | | | | | | | | | | | | 40.00 |
| Ethanol | | | | | | | | | | | | | | |
| DH$_2$O | 19.25 | 19.25 | 19.40 | 40.00 | 19.70 | 39.10 | 40.00 | 19.70 | 40.00 | 19.70 | 40.00 | 19.70 | 19.95 | |
| Suttocide | | | | | | | | | | | | | | |
| CMC 7MXF | 0.50 | 0.5* | 0.40 | | 0.30 | 0.90 | | 0.30 | | 0.30 | | | | |
| Natrosol 250H[a] | | | 0.20 | | | | | | | | | | | |
| Xanthan Gum | | | | | | | | | | | | 0.20 | | |
| klucel GF NF | | | | | | | | | | | | | | 1.00 |
| Carrageenan TPC1 | | | | | | | | | | | | | | |
| Sylodent 15 | | | | | | | | | | | | | | |
| SMFP | 1.00 | 1.00* | | | | | | | | | | | | |
| Baking Soda | | | | | 30.00 | | 30.00 | 60.00 | 60.00 | | | | | |
| Sylodent 700[b] | | | | | | | | | | 5.00 | 5.00 | | | |
| ETD 2020**[c] | | | | | | | | | | | | | 0.05 | |
| Dical[d] | 60.00 | 60.00* | 60.00 | 60.00 Control | 30.00 | 60.00 | 30.00 Control | | | 55.00 Control | 55.00 | 60.00 | 60.00 | 60.00 |

*dry-blend prior to adding to the solvent system
**ETD 2020 may not fully dissolve in gel phase - mixture until lump free. It should fully dissolve in the slurry phase
[a]Natrosol ® 250H: Hydroxyethylcellulose with 1.0% viscosity 1500 to 2500 cps Brookfield LVT, 30 rpm a5 25° C. Marketed by Hercules Incorporated.
[b]Sylodent 700: Amorphous Silica from W.R. Grace, Baltimore, Maryland.
[c]ETD 2020: Acrylates/C10-33 alkyl acrylate crosspolymer from B F Goodrich, Cleveland, Ohio.
[d]Dical: Abrasive, dicalcium phosphate dihydrate.

TABLE 8

Abrasive Suspension Formulations

| EX. | Days Stored | Condition | pH | *Viscosity (cP) At rest/after mixing | Comments/Observations |
|---|---|---|---|---|---|
| 20 | 1 | RT | 6.77 | 96,600/21,860 | Smooth, uniform, no settling, no gel structure. |
| | 2 | RT | 6.81 | 103,500/23,960 | Smooth, uniform, no settling, no gel structure. |
| | 7 | RT | 6.84 | 197,000/24,300 | Smooth, uniform, no settling, no gel structure. |
| 21 | 1 | RT | 6.66 | 79,200/19,300 | Smooth, uniform, no settling, no gel structure. |
| | 2 | RT | 6.82 | 49,600/19,000 | Smooth, uniform, no settling, no gel structure. |
| | 7 | RT | 6.74 | 101,200/19,700 | Smooth, uniform, no settling, no gel structure. |
| 22 | 1 | RT | 6.87 | 194,600/48,300 | Smooth, uniform, no settling, more structured. |
| | 2 | RT | 7.12 | 161,000/47,900 | Smooth, uniform, no settling, more structured. |
| | 7 | RT | 7.37 | 108,000/40,460 | Smooth, uniform, no settling, more structured. |
| 23 Control | 1 | RT | 7.37 | 69,800/5160 | ~10% syneresis, sludgy with some settling. |
| | 2 | RT | 7.26 | 67,600/6500 | ~10% syneresis, sludgy with some settling. |
| | 7 | RT | 7.26 | 76,500/7500 | ~10% syneresis, sludgy with some settling. |
| 24 | 1 | RT | 8.29 | 73,300/5500 | Smooth, uniform, no settling, no gel structure. |
| | 2 | RT | 8.18 | 13,800/4733 | Smooth, uniform, no settling, no gel structure. |
| | 7 | RT | 7.97 | 9300/2960 | ~1% syneresis, clear supernatant, sludgy. |
| 25 | 1 | RT | 7.61 | 73,100/13,400 | Smooth, uniform, no settling, no gel structure. |
| | 2 | RT | 7.64 | 22,600/12,000 | Smooth, uniform, no settling, no gel structure. |
| | 7 | RT | 7.46 | 16,300/8600 | Smooth, uniform, no settling, no gel structure. |
| 26 Control | 1 | RT | 7.79 | 44,000/0 | ~15% syneresis, clear supernatant, sludgy. |
| | 2 | RT | 7.89 | 32,800/0 | ~15% syneresis, clear supernatant, sludgy. |
| | 7 | RT | 7.93 | 396,000/0 | ~20% syneresis, clear supernatant, sludgy, settling. |
| 27 | 1 | RT | 8.49 | 73,000/0 | ~25% syneresis, clear supernatant, sludgy. |
| | 2 | RT | 8.71 | 44,600/0 | ~25% syneresis, clear supernatant, sludgy. |
| | 7 | RT | 8.59 | 111,000/0 | ~25% syneresis, clear supernatant, sludgy. |
| 28 Control | 1 | RT | 8.51 | 108,000/0 | ~25% syneresis, clear supernatant, sludgy. |
| | 2 | RT | 8.84 | 56,600/0 | ~25% syneresis, clear supernatant, sludgy. |
| | 7 | RT | 8.73 | 95,000/0 | ~25% syneresis, clear supernatant, sludgy. |
| 29 | 1 | RT | 6.96 | 40,500/10,600 | Smooth, uniform, no settling, no gel structure. |
| | 2 | RT | 7.01 | 29,600/11,700 | Smooth, uniform, no settling, no gel structure. |
| | 7 | RT | 7.62 | 24,800/11,000 | Smooth, uniform, no settling, no gel structure. |
| 30 Control | 1 | RT | 7.20 | 111,000/5260 | ~5% syneresis, clear supernatant, sludgy. |
| | 2 | RT | 7.18 | 86,200/5200 | ~10% syneresis, clear supernatant, sludgy. |
| | 7 | RT | 7.10 | 217,000/32,400 | ~10% syneresis, clear supernatant, sludgy. |
| 31 | 1 | RT | 6.85 | 46,300/12,460 | Smooth, uniform, no settling, no gel structure. |
| | 2 | RT | 6.98 | 27,500/11,500 | Smooth, uniform, no settling, no gel structure. |
| | 7 | RT | 7.30 | 167,600/36,700 | Smooth, uniform, no settling, no gel structure. |
| 32 | 1 | RT | 6.71 | 155,000/10,500 | ~1% syneresis, clear supernatant, sludgy. |
| | 2 | RT | 6.72 | 44,500/10,960 | ~10% syneresis, clear supernatant, sludgy. |
| | 7 | RT | 6.88 | 149,000/13,500 | ~10% syneresis, clear supernatant, sludgy. |
| 33 | 1 | RT | 5.76 | 171,800/81,000 | Glossy, stringy, uniform, visible gels. |
| | 2 | RT | 5.87 | 128,500/75,600 | Glossy, stringy, uniform, visible gels. |
| | 7 | RT | 5.92 | 127,600/78,800 | Glossy, stringy, uniform, visible gels. |

*Syneresis is measured by volume.

Example 20 evaluated dicalcium phosphate dihydrate (dical) at 60-wt % in a 50/50 mixture of Sorbo and water with 0.50 wt % CMC 7MXF and 1.00 wt % sodium monofluorophosphate (SMFP). The resulting suspension was uniform, however, the viscosity was 104,000 cP @ 2 days and viscosity gain was observed with time.

Example 21 evaluated dical at 60 wt % in a 25/25/50 mixture of Sorbo, glycerin, and water with 0.50 wt % CMC 7MXF and 1.00 wt % SMFP dry-blended into the abrasive. The resulting suspension was uniform and stable. The viscosity was about 50,000 cP at 2 days and viscosity gain was observed with time.

Example 22 evaluated dical at 60-wt % in a 25/25/50 mixture of Sorbo, glycerin, and water with 0.40 wt % CMC 7MXF and 0.20 wt % Natrosol® 250H. The resulting suspension was uniform and the viscosity was about 161,000 cP at 2 days.

Example 23 was a control and evaluated dical at 60-wt % in a polymer free aqueous system. As expected, settling of the abrasive occurred immediately.

Example 24 evaluated dical and baking soda at 30-wt % each in a 25/25/50 mixture of Sorbo, glycerin, and water, with 0.30 wt % CMC 7MXF. The resulting suspension was uniform for 2 days but then began to settle. The viscosity of this Example was about 14,000 cP at 2 days.

Example 25 evaluated dical at 60-wt % in an aqueous system with 0.90 wt % CMC 7MXF. The resulting suspension was uniform, and the viscosity was about 23,000 cP at 2 days.

Example 26 was a control and evaluated dical and sodium bicarbonate at 30-wt % each in a polymer free 100% aqueous system. As expected, settling occurred immediately.

Example 27 evaluated sodium bicarbonate at 60-wt % in a 25/25/50 mixture of Sorbo, glycerin, and water, with 0.30 wt % CMC 7MXF. Settling of the abrasive occurred immediately with the polymer more than likely salting out.

Example 28 control evaluated sodium bicarbonate at 60-wt % in a polymer free 100% aqueous system. As expected, the abrasive settled immediately.

Example 29 evaluated dical and sodium bicarbonate at 55 wt % and 5-wt %, respectively. The solvent system was a 25/25/50 mixture of Sorbo®, glycerin, and water, with 0.30 wt % CMC 7MXF. The resulting suspension was uniform and the viscosity was about 30,000 cP at 2 days.

Example 30 control evaluated dical and sodium bicarbonate at 55 wt % and 5 wt %, respectively, in a polymer free 100% aqueous system. As expected, settling of the abrasive occurred immediately.

Example 31 evaluated dical at 60 wt % in a 25/25/50 mixture of Sorbo, glycerin, and water, with 0.20 wt % Xanthan gum. The resulting suspension was uniform and the viscosity was about 28,000 cP at 2 days.

Example 32 evaluated dical at 60 wt % in a 50/50 mixture of Sorbo and water with 0.05 wt % Carbopol ETD 2020. The resulting suspension began settling within a day.

Example 33 evaluated dical at 60 wt % in a 100% propylene glycol system with 1.00 wt % Klucel GF NF. The resulting suspension was glossy, stringy, and uniform, and the viscosity was about 130,000 cP at 2 days. This system was stable after 6 month's storage at room temperature.

In summary, the addition of water-soluble, water-swellable polymers (WSPs) improves the suspension of abrasives in various solvent systems.

TABLE 9

Abrasive Suspension Formulations

| | Example No. | | | | | | | | | | |
|---|---|---|---|---|---|---|---|---|---|---|---|
| | 34 | 35 | 36 | 37 | 38 | 39 | 40 | 41 | 42 | 43 | 44 |
| Sorbo | 20.00 | 20.00 | 20.00 | | 20.00 | 20.00 | 20.00 | 10.00 | | 14.50 | 14.90 |
| Glycerin | | | | | | | | 10.00 | | | |
| Carbowax ® 200[a] | | | | | | | | | | | |
| Propylene glycol | | | | | | | | | 39.00 | | |
| Ethanol | | | | | | | | | | | |
| DH$_2$O | 19.00 | 19.50 | 19.00 | 39.50 | 19.50 | 19.20 | 19.00 | 19.95 | | 14.60 | 14.60 |
| Suttacide | 0.50 | | 0.50 | 0.50 | 0.50 | 0.50 | 0.50 | 0.00 | | 0.50 | 0.50 |
| CMC 7MXF | 0.30 | 0.30 | 0.30* | | | | 0.30 | | | 0.20 | |
| Xanthan Gum[b] | | | | | | | | | | | |
| Kelco ® K6B166 | | | | | | | | | | | |
| ETD 2020** | | | | | | | | 0.05 | | | |
| Klucel ® GF NF | | | | | | | | | 1.00 | | |
| Genuvisco ® TPC1 | | | | | | 0.20 | | | | | |
| Sylodent ® 15 | | | | | | | | 0.10 | | | |
| SMFP | | | | | | | | | | | |
| PCC2[c] | 60.00 | 60.00 | 60.00* | 60.00 Control | 60.00 Control | 60.00 | 60.00 | 60.00 | 60.00 | 70.00 | 70.00 Control |

[a]Polyethylene glycol from Union Carbide
[b]From Kelco ® K6B166
[c]PCC2: This is a precipitated C$_a$CO$_3$ having a density of 0.45 grams/ml
*dryblend prior to adding to the solvent system
**ETD 2020 did not fully dissolve in gel phase - mixed until lump free. It fully dissolved in the slurry phase

TABLE 10

Abrasive Suspension Formulations

| Example 6 | Days Stored | Condition | pH | *Viscosity(cP) At rest/after mixing | Comments/Observations |
|---|---|---|---|---|---|
| 34 | 1 | RT | 9.17 | 152,000/4330 | No settling, gel-like structure. Shear thinned easily. |
| | 2 | RT | 9.21 | 85,000/2270 | No settling, weaker gel-like structure. Shear thinned easily. |
| | 7 | RT | 9.74 | 114,000/4667 | No settling, weaker gel-like structure. Shear thinned easily. |
| 35 | 1 | RT | 7.71 | 416,000/7400 | No settling, gel-like structure. Shear thinned easily. |
| | 2 | RT | 7.76 | 214,000/3600 | No settling, weaker gel-like structure. Shear thinned easily. |
| | 7 | RT | 8.72 | 51,760/4000 | No settling, weaker gel-like structure. Sl. Syneresis. Shear thinned easily. |
| 36 | 1 | RT | 9.13 | 100,000/2500 | No settling, gel-like structure. Shear thinned easily. |
| | 2 | RT | 9.10 | 62,000/2100 | No settling, weaker gel-like structure. Shear thinned easily. |
| | 7 | RT | 9.67 | 75,000/2167 | No settling, weaker gel-like structure. Shear thinned easily. |
| 37 Control | 1 | RT | 9.32 | 423,000/189,000 | ~1% syneresis, sludgy thruout Example. |
| | 2 | RT | 9.36 | 385,000/342,000 | ~1% syneresis, sludgy thruout Example. |
| | 7 | RT | 10.00 | 388,000/343,000 | ~1% syneresis, sludgy thruout Example. |

TABLE 10-continued

Abrasive Suspension Formulations

| Example 6 | Days Stored | Condition | pH | *Viscosity(cP) At rest/after mixing | Comments/Observations |
|---|---|---|---|---|---|
| 38 Control | 1 | RT | 9.05 | 446,000/427,000 | Very slight syneresis, sludgy thruout. |
| | 2 | RT | 9.12 | 426,000/386,000 | Very slight syneresis, sludgy thruout. |
| | 7 | RT | 9.62 | 461,000/446,000 | Slight syneresis, sludgy thruout. |
| 39 | 1 | RT | 9.16 | 391,000/18,700 | Very slight syneresis, sludgy thruout. |
| | 2 | RT | 9.19 | 47,000/13,900 | Very slight syneresis, sludgy thruout. |
| | 7 | RT | 9.69 | 54,000/15,600 | Slight syneresis, sludgy thruout. |
| 40 | 1 | RT | 9.49 | 437,000/28,400 | No settling, gel-like structure. Shear thinned easily. |
| | 2 | RT | 9.54 | 356,00/23,600 | No settling, gel-like structure. Shear thinned easily. |
| | 7 | RT | 9.40 | 308,000/32,400 | No settling, gel-like structure. Shear thinned easily. |
| 41 | 1 | RT | | | Example too heavy to incorporate all the abrasive. |
| | 2 | RT | | | |
| | 7 | RT | | | |
| 42 | 1 | RT | 8.12 | 540,000/319,000 | No settling, stringy texture, skinned surface, very glossy. |
| | 2 | RT | 8.48 | 324,000/204,000 | No settling, stringy texture, skinned surface, very glossy. |
| | 7 | RT | 8.20 | 459,000/285,000 | No settling, stringy texture, skinned surface, very glossy. |
| 43 | 1 | RT | | | Example too heavy to incorporate all the abrasive. |
| | 2 | RT | | | |
| | 7 | RT | | | |
| 44 | 1 | RT | | | Example too heavy to incorporate all the abrasive. |
| | 2 | RT | | | |
| | 7 | RT | | | |

Example 34 evaluated PCC2 at 60 wt % in a 50/50 mixture of Sorbo® and water with 0.30 wt % CMC 7MXF. The resulting suspension was uniform with a gel-like structure and the viscosity of this Example was about 85,000 cP at 2 days.

Example 35 evaluated PCC2 at 60 wt % in the same system as Examkple 34 but without preservative. The resulting suspension was uniform with a gel-like structure and the viscosity of this Example was about 214,000 cP at 2 days. The pH of this system was lower compared to that of the preservative containing Example.

Example 36 evaluated PCC2 at 60 wt % in a 50/50 mixture of Sorbo® and water with 0.30 wt % CMC 7MXF dry-blended in the abrasive. The resulting suspension was uniform with a gel-like structure and the viscosity of this Example was about 62,000 cP at 2 days.

Example 37 control evaluated PCC2 at 60 wt % in a polymer free 100% aqueous system. As expected, scuttling occurred immediately with the resulting Example being very sludgy.

Example 38 control evaluated PCC2 at 60 wt % in a 50/50 mixture of Sorbo and water. The resulting Example demonstrated slight syneresis and was very viscous, about 426,000 cP at 2 days, and sludgy.

Example 39 evaluated PCC2 at 60 wt % in a 50/50 mixture of Sorbo and water with 0.20 wt % Genuvisco® TPC-1 carrageenan. The resulting Example demonstrated slight syneresis and significantly lower viscosity (47,000 cP at 2 days, and sludgy) compared to example 38 without the polymer.

Example 40 evaluated PCC2 at 60 wt % in a 50/50 mixture of Sorbo and water with 0.30 wt % CMC 7MXF and 0.10 wt % Sylodent 15 (hydrated silica). The resulting suspension was uniform with a gel-like structure. The viscosity of this Example was about 356,000 cP at 2 days.

Example 41 evaluated PCC2 at 60 wt % in a 25/25/50 mixture of Sorbo®, glycerin, and water, with 0.05 wt % Carbopol® ETD 2020. This Example became too heavy to mix and not all of the abrasive could be added.

Example 42 evaluated PCC2 at 60 wt % in a 100% propylene glycol system with 1.00 wt % Klucel® GF NF. The resulting suspension was uniform, glossy, and stringy, with a skinned surface. The viscosity of this Example was about 324,000 cP at 2 days. This is an example of in anhydrous fluidized abrasive suspension. That is no water was used as one of the vehicle.

Example 43 evaluated PCC2 at 70 wt % in a 50/50 mixture of Sorbo and water with 0.20 wt % CMC 7MXF. This Example became too heavy to mixture and not all of the abrasive could be added.

Example 44 control evaluated PCC2 at 70 wt % in a polymer free mixture of 50/50 Sorbo and water. This Example became too heavy to mixture and not all of the abrasive could be added.

| Bulk Densities of Dical and PCC Abrasive | |
|---|---|
| Example | Bulk Density g/mls |
| PCC2 | 0.422–0.447 |
| PCC1 | 0.834 |
| Dical | 0.757 |

In summary, the addition of WSPs improves the suspension of the PCC2 abrasive (bulk density 0.422–0.447) in dentifrice solvents. Up to 65 wt % abrasive could be used in the suspension systems.

Using the higher bulk density PCC 1 (0.834) suspensions with higher abrasive loading were achieved than with the lower bulk density PCC2 (0.422–0.447).

TABLE 11

Fluidized Abrasive Suspension Formulations

| Example | 45 | 46 | 47 |
|---|---|---|---|
| Sorbo ® (70%) | 29.38 | 30.00 | 19.95 |
| DH$_2$O | 29.38 | 30.0 | 19.95 |
| CMC 7MXF | 1.0* | | |
| Xanthan Gum | 0.25* | | |
| Ultrez ® 10 | | | 0.1* |
| Dical | | | 60.0* |
| Syledent ® 9*** | 40* | 40 Control | |

*Dry-blend prior to adding to the solvent system
**Ultrez 10 is cross-linked acrylic acid polymer, marketed by BF Goodrich of Cleveland, Ohio. Ultrez did not fully dissolve in gel phase-mixted until lump free. It fully dissolved in the slurry phase
***Syledent 9 is abrasive silica from Degusaa of Frankfurt, Germany

TABLE 12

Abrasive Slurry with Cationic Guar/CMC 7MXF
Example 48

Phase 1

| 9.825% | Sorbitol |
|---|---|
| 9.825% | DH$_2$O |
| 0.5% | Sutticide A |
| | Premix them |
| 0.1% | CMC 7MXF |
| | Stirred until homogeneously mixed with no lumps observed |

Phase 2

| 9.825% | Sorbo ® |
|---|---|
| 9.825% | DH$_2$O |
| | Premix them |
| 0.1% | N-Hance ® 3000 |
| | Mixture for 5 minutes |
| | Add citric acid to lower pH to between 5 to 7. |
| | Stirred until homogeneous with no lumps observed |

Procedure

| | Phase 1 & Phase 2 were mixed together and stirred until Homogeneous |
|---|---|
| 60.0% | Added PCC2 with Bulk Density of 0.447 And mixed until Homogeneous |

N-Hance 3000: is cationic guar with 1.0% concentration aqueous Brookfield viscosity of 3000 to 4000 cps at 25° C. It is marketed by Hercules Incorporated.

Example 45 evaluated abrasive silica Sident® 9 at 40 wt % in a 50/50 mixture of Sorbo® and water with 1.00 wt % CMC 7MXF and 0.25 wt % Xanthan gum dry-blended into the abrasive. The resulting suspension was uniform with the viscosity of 260,000 cP at 2 days.

Example 46 control evaluated Sident 9 at 40 wt % in a polymer free mixture of 50/50 Sorbo and water. Settling of the abrasive was observed at one day.

Example 47 evaluated dical at 60 wt % in a 50/50 mixture of Sorbo and water with 0.10 wt % Carbopol Ultrez 10 dry-blended into the abrasive. Settling of the abrasive was observed at one day with the Example becoming sludgy.

Example 48 evaluated PCC2 at 60 wt % in a 50/50 mixture of Sorbo and water with 0.10 wt % CMC 7MXF and 0.10 wt % N-HANCE® 3000. The resulting suspension was uniform, very viscous (825,000 cP @ 2 days), and gel-like. This suspension shear thinned very easily.

In summary, anionic/cationic polymer systems can be used to suspend toothpaste abrasives. Silica abrasive can be suspended with water-soluble/water-swellable polymers (WSPs).

EXAMPLE 49

Model Cream Toothpaste with CMC 7MXF/PCC Suspension

| | Ingredient | % M | wt(g) |
|---|---|---|---|
| I. | CMC 7MX | 7.95[1] | 15.05 |
| | Glycerine 100% | | 110.00 |
| | Sorbo ® | | 187.20 |
| | Distilled water | | 119.15 |
| II. | PCC Suspension (Example 7) | | 1500.00 |
| III. | Tetra sodium pyrophosphate (TSPP) | | 8.40 |
| | Sodium saccharin (SC) | | 4.00 |
| | Sodium monofluorophosphate (SMFP) | | 15.20 |
| | Sodium benzoate (SB) | | 10.00 |
| IV. | Flavor | | 11.00 |
| | Sodium lauryl sulfate (SLS) | | 20.00 |
| | | | 2000.00 |

[1]Wt. % moisture in CMC.

Procedure:

1) While wearing protective gloves, dry ice was added to the vacuum traps of the Ross mixer.
2) Part I. Glycerine was weighed into a 1.5 liter beaker. CMC was dispersed in glycerine while stirring (use

TABLE 13

Toothpaste
Fluidized Abrasive Suspension Formulations

| Example | Days Stored | Condition | pH | *Viscosity (cP) At rest/After mixture | Comments/Observations |
|---|---|---|---|---|---|
| 45 | 1 | RT | 6.24 | 398,000/116,000 | Smooth, uniform, no gel structure, no settling. |
| | 2 | RT | 6.18 | 260,000/89,500 | Smooth, uniform, no gel structure, no settling. |
| | 7 | RT | 6.22 | 421,000/96,700 | Smooth, uniform, no gel structure, no settling. |
| 46 Control | 1 | RT | 6.28 | 145,000/24,200 | ~10% syneresis, clear supernatant, some settling. |
| | 2 | RT | 6.23 | 118,000/0 | ~15% syneresis, clear supernatant, some settling. |
| | 7 | RT | 6.21 | 426,000/0 | ~20% syneresis, clear supernatant, some settling. |
| 47 | 1 | RT | 6.34 | 1,600,000/406,000 | ~1% syneresis, sludgy, some settling. |
| | 2 | RT | 6.34 | 426,000/61,300 | ~3% syneresis, sludgy, some settling. |
| | 7 | RT | 6.38 | 1,360,000/155,000 | ~5% syneresis, sludgy, some settling. |
| 48 | 1 | RT | 6.45 | 1,520,000/64,600 | Very heavy, uniform, gel-like, shear thinned easily. |
| | 2 | RT | 6.58 | 825,000/165,000 | Very heavy, uniform, gel-like, shear thinned easily. |
| | 7 | RT | 6.66 | 1,270,000/167,000 | Very heavy, uniform, gel-like, shear thinned easily. | prop type agitator, 2/shaft). Stirred for 5 minutes or until adequately dispersed. Sorbo product was added and continued stirring for another 10 minutes. Water was added and stirred for 15 to 30 minutes making sure the polymer was completely hydrated (no gels). Part I was transferred to toothpaste mixer (Ross double planetary mixer).

3) Part II. The suspension was added to the Ross mixer and mixed for 5 min. at a low speed. Mixer was opened and agitators and vessel walls were scraped down. Mixer was sealed and vacuum was applied. Mixer was then run at high speed under vacuum for 10 minutes or until smooth.

4) Part III. Dry salts were added to the Ross mixer and mixed for 20 minutes at low speed without vacuum.

5) Part IV. The SLS was added and mixed for 5 minutes at low speed without vacuum. Then Flavor was added and mixed for 2 min. at low speed. The mixer was opened and the agitators and vessel walls were scraped down. The mixer was then closed and a vacuum was applied. The mixer was turned on and mixed at medium speed for 10 minutes; foaming was observed.

6) The mixer speed was gradually reduced and shut off and the mixer was opened. The toothpaste was packed out into tubes and jars.

EXAMPLE 50

Model Cream Toothpaste with CMC 7MXF/PCC Suspension Glycerin Free Formulation

| | Ingredient | % M (moisture) | wt(g) |
| --- | --- | --- | --- |
| I. | CMC 7MXF | 7.95[1] | 12.05 |
| | Sorbo ® | | 408.63 |
| | Distilled water | | 10.72 |
| | Sodium benzoate | | 10.00 |
| II. | PCC Suspension (Example 6) | | 1500.00 |
| III. | Tetra sodium pyrophosphate | | 8.40 |
| | Sodium saccharin | | 4.00 |
| | Sodium monofluorophosphate | | 15.20 |
| IV. | Flavor | | 11.00 |
| | Sodium lauryl sulfate | | 20.00 |
| | | | 2000.00 |

[1]Wt. % moisture in CMC.

Procedure:

1) While wearing protective gloves, dry ice was added to the vacuum traps of the Ross mixer.

2) Part I. Sorbo was weighed into a 1.5 liter beaker. Water and then sodium benzoate were added to the beaker and stirred for 15 minutes. CMC was then add to the Sorbo/water/salt mixture while stirring (used prop type agitator, 2/shaft). The beaker was stirred for 30 minutes or until CMC fully hydrated. This Part I was transferred to a toothpaste mixer (Ross double planetary mixer).

3) Part II. This suspension was added to the Ross mixer and mixed for 5 min. at a low speed. The mixer was then opened and the agitators and vessel walls were scraped down. The mixer was closed and a vacuum was applied. This formulation was mixed on high speed under vacuum for 10 minutes or until smooth.

4) Part III. The dry salts were added to the Ross mixer and mixed for 20 minutes at low speed without vacuum.

5) Part IV. The SLS was added and mixed for 5 minutes at low speed without vacuum. Flavor was then added and mixed for 2 min. at low speed. The mixer was opened and the agitators and vessel walls were scraped down. The mixer was then closed and a vacuum was applied. The mixer was run at medium speed for 10 minutes, observing for foaming.

6) The mixer's speed was gradually reduced and finally the mixer was shut off and the vacuum was broken. The paste was packed out to tubes and jars.

EXAMPLE 51

Control

Model Cream Toothpaste with CMC 7MXF Glycerine Free Formulation

| | Ingredient | % M | Wt(g) |
| --- | --- | --- | --- |
| I. | CMC 7MXF | 7.95[1] | 19.55 |
| | Sorbo ® | | 708.60 |
| | Distilled water | | 178.25 |
| II. | Precipitated CaCO$_3$, (PCC2Bulk density 0.447 g/ml) (Dry powder) | | 900.00 |
| III. | Tetra sodium pyrophosphate | | 8.40 |
| | Sodium saccharin | | 4.00 |
| | Sodium monofluorophosphate | | 15.20 |
| | Sodium benzoate | | 10.00 |
| | Distilled water | | 125.00 |
| IV. | Flavor | | 11.00 |
| | Sodium lauryl sulfate | | 20.00 |
| | | | 2000.00 |

[1]Wt. % moisture in CMC.

Procedure

1) Begin with Part III. The salts were added to the water while stirring, heated to ~60° C. to dissolve, and covered to prevent moisture loss during heating.

2) Part I. Sorbo product was weighed into a 1.5 liter beaker. CMC was mixed with the Sorbo product while stirring and stirred for 15 minutes or until adequately dispersed. Then water was added and stirred for 15 to 30 minutes making sure the polymer was completely hydrated (no gels). Warm salt solution was then added while stirring and continued stirring for 15 minutes or until homogeneous (no lumps or gels). This Part I was transferred to a toothpaste mixer (Ross double planetary mixer).

3) Part II. PCC2 dry was added to the Ross mixer and mixed for 10 min. at a low speed to completely wet the PCC2. The mixer was opened and the beaters and bowl sides were scraped down. The mixer was closed and vacuum was applied. The mixer was run on high speed under vacuum for 20 minutes or until smooth.

4) Part IV. SLS was added and mixed for 5 minutes at low speed without vacuum. Flavor was added and mixed for 2 min. at low speed. The mixer was opened and beaters and bowl sides were scraped down. The mixer was closed and a vacuum was applied. The mixer was run at medium speed for 15 minutes, observing for foaming.

5) The mixer's speed was gradually reduced and the mixer was finally shut off and the vacuum was broken. The toothpaste was packed out into jars.

EXAMPLE 52

Model Cream Toothpaste with CMC 7MXF/PCC Suspension Glycerin Free Formulation

| | Ingredient | % M | wt(g) |
|---|---|---|---|
| I. | CMC 7MX | 7.95[1] | 12.05 |
| | Sorbo | | 408.63 |
| | Distilled water | | 10.72 |
| | Sodium benzoate | | 10.00 |
| II. | PCC Suspension (Example 52A) | | 1500.00 |
| III. | Tetra sodium pyrophosphate | | 8.40 |
| | Sodium saccharin | | 4.00 |
| | Sodium monofluorophosphate | | 15.20 |
| IV. | Flavor | | 11.00 |
| | Sodium lauryl sulfate | | 20.00 |
| | | | 2000.00 |

[1]Wt. % moisture in CMC.

Procedure

1) While wearing protective gloves, dry ice was added to the vacuum traps of the Ross mixer.
2) Part I. Sorbo product was weighed into a 1.5 liter beaker. Water and then sodium benzoate were added to the beaker and stirred for 15 minutes. CMC was then add to the Sorbo/water/salt mixture while stirring (used prop type agitator, 2/shaft). The beaker was stirred for 30 minutes or until fully hydrated. This Part I was transferred to a toothpaste mixer (Ross double planetary mixer).
3) Part II. This suspension was added to the Ross mixer and mixed for 5 min. at a low speed. The mixer was then opened and the agitators and vessel walls were scraped down. The mixer was sealed and a vacuum was applied. This formulation was mixed on high speed under vacuum for 10 minutes or until smooth.
4) Part III. The dry salts were added to the Ross mixer and mixed for 20 minutes at low speed without vacuum.
5) Part IV. The SLS was added and mixed for 5 minutes at low speed without vacuum. Flavor was then added and mixed for 2 min. at low speed. The mixer was opened and the agitators and vessel walls were scraped down. The mixer was then closed and a vacuum was applied. The mixer was run at medium speed for 10 minutes, observing for foaming.
6) The mixer's speed was gradually reduced and finally the mixer was shut off and the vacuum was broken. The paste was packed out to tubes and jars.

EXAMPLE 52A

Preparation PCC2 FAS for Example 52

| Sorbo ® | 20.00 wt % |
|---|---|
| Dist. water | 19.00 |
| CMC 7MXF | 00.05 |
| Suttocide ® A | 00.50 |
| PCC2 | 60.00 |

The suspension was prepared by using Procedure 1

EXAMPLE 53

Model Cream Toothpaste with CMC 7MXF/Abrasive Suspension

| | Ingredient | % M | wt(g) |
|---|---|---|---|
| I. | CMC 7MXF | 7.95[1] | 15.42 |
| | Glycenne 100% | | 110.00 |
| | Sorbo ® | | 187.20 |
| | Distilled water | | 118.78 |
| II. | Dical/Syledent ® 700 Suspension (Example 29) | | 1500.00 |
| III. | Tetra sodium pyrophosphate | | 8.40 |
| | Sodium saccharin | | 4.00 |
| | Sodium monofluorophosphate | | 15.20 |
| | Sodium benzoate | | 10.00 |
| IV. | Flavor | | 11.00 |
| | Sodium lauryl sulfate | | 20.00 |
| | | | 2000.00 |

[1]Wt. % moisture in CMC.

Procedure:

1) While wearing protective gloves, dry ice was added to the vacuum traps of the Ross mixer.
2) Part I. Glycerine was weighed into a 1.5 liter beaker. CMC, Sorbo® product, and then water were added to the beaker and stirred for 15 minutes. The beaker was stirred for 30 minutes or until fully hydrated. This Part I was transferred to a toothpaste mixer (Ross double planetary mixer).
3) Part II. This suspension was added to the Ross mixer and mixed for 5 min. at a low speed. The mixer was then opened and the agitators and vessel walls were scraped down. The mixer was sealed and a vacuum was applied. This formulation was mixed on high speed under vacuum for 10 minutes or until smooth.
4) Part III. The dry salts were added to the Ross mixer and mixed for 20 minutes at low speed without vacuum.
5) Part IV. The SLS was added and mixed for 5 minutes at low speed without vacuum. Flavor was then added and mixed for 2 min. at low speed. The mixer was opened the agitators and vessel walls were scraped down. The mixer was then closed and a vacuum was applied. The mixer was run at medium speed for 10 minutes, observing for foaming.
5) The mixer's speed was gradually reduced and finally the mixer was shut off and the vacuum was broken. The paste was packed out to tubes and jars.

EXAMPLE 54

Model Cream Toothpaste with Xanthan Gum/Abrasive Suspension

| | Ingredient | % M | wt(g) |
|---|---|---|---|
| I. | Xanthan Gum | 11.94[1] | 10.99 |
| | Glycerine 100% | | 110.00 |
| | Sorbo | | 187.20 |
| | Distilled water | | 123.21 |
| II. | Dical Suspension (Example 31) | | 1500.00 |
| III. | Tetra sodium pyrophosphate | | 8.40 |
| | Sodium saccharin | | 4.00 |
| | Sodium monofluorophosphate | | 15.20 |
| | Sodium benzoate | | 10.00 |

-continued

Model Cream Toothpaste with Xanthan Gum/Abrasive Suspension

| | Ingredient | % M | wt(g) |
|---|---|---|---|
| IV. | Flavor | | 11.00 |
| | Sodium lauryl sulfate | | 20.00 |
| | | | 2000.00 |

[1]Wt % moisture in xanthan gum.

Procedure:

1) While wearing protective gloves, dry ice was added to the vacuum traps of the Ross mixer.
2) Part I. Glycerine was weighed into a 1.5l beaker. Xanthan gum, Sorbo® product, and then water were added to the beaker and stirred for 15 minutes. The beaker was stirred for 30 minutes or until fully hydrated. This Part I was transferred to a toothpaste mixer (Ross double planetary mixer).
3) Part II. This suspension was added to the Ross mixer and mixed for 5 minutes at a low speed. The mixer was then opened and the agitators and vessel walls were scraped down. The mixer was closed and a vacuum was applied. This formulation was mixed on high speed under vacuum for 10 minutes or until smooth.
4) Part III. The dry salts were added to the Ross mixer and mixed for 20 minutes at low speed without vacuum.
5) Part IV. The SLS was added and mixed for 5 minutes at low speed without vacuum. Flavor was then added and mixed for 2 min. at low speed. The mixer was opened the agitators and vessel walls were scraped down. The mixer was then closed and a vacuum was applied. The mixer was run at medium speed for 10 minutes, observing for foaming.
6) The mixer's speed was gradually reduced and finally the mixer was shut off and the vacuum was broken. The paste was packed out to tubes and jars.

TABLE 14

Model Cream Toothpaste Stability Data - Evaluation of Abrasive Slurries

| Example | Days Stored | Viscosity (cP) × 1000 | | | Cuban Value | | String Value (sec) |
|---|---|---|---|---|---|---|---|
| | | RT | 40° C. | 5° C. | RT | 40° C. | |
| 49 | 1 | 272 | 323 | 241 | 6 | 7 | — |
| | 7 | 365 | 361 | 314 | 7 | 7 | 65.9 |
| | 14 | 378 | 367 | 325 | 7 | 7 | — |
| | 30 | 490 | 504 | 484 | 9.5 | 10 | — |
| | 60 | 534 | 530 | 505 | 10 | 10 | — |
| | 90 | 535 | 530 | 500 | 10 | 10 | — |
| | 6 mos. | | | | | | — |
| | 9 mos. | | | | | | — |
| | 12 mos. | | | | | | — |
| 50 | 1 | 259 | 357 | 230 | 4 | 4 | — |
| | 7 | 336 | 419 | 320 | 6 | 6.5 | 66.9 |
| | 14 | 381 | 388 | 357 | 8.5 | 6 | — |
| | 30 | 496 | 514 | 482 | 10.5 | 9 | — |
| | 60 | 528 | 539 | 496 | 10 | 10 | — |
| | 90 | 532 | 553 | 505 | 10 | 10 | — |
| | 6 mos. | | | | | | — |
| | 9 mos. | | | | | | — |
| | 12 mos. | | | | | | — |
| 51 Control | 1 | 754 | 823 | 772 | 6 | 7 | — |
| | 7 | 910 | 926 | 868 | 7 | 8.5 | 68.1 |
| | 14 | 1125 | 1097 | 1062 | 10 | 10.5 | — |
| | 30 | 1218 | 1175 | 1140 | 11.5 | 10 | — |
| | 60 | 1395 | 1347 | 1178 | 12 | 11.5 | — |
| | 90 | 1537 | 1268 | 1098 | 11.5 | 10.5 | — |
| | 6 mos. | | | | | | — |
| | 9 mos. | | | | | | — |
| | 12 mos. | | | | | | — |
| 52 | 1 | 486 | 490 | 507 | 4.5 | 4.5 | — |
| | 7 | 542 | 503 | 582 | 7 | 6 | 66 |
| | 14 | 590 | 567 | 554 | 7 | 8 | — |
| | 30 | 595 | 575 | 624 | 7 | 8 | — |
| | 60 | 635 | 634 | 644 | 7.5 | 8 | — |
| | 90 | 582 | 598 | 581 | 7 | 8 | — |
| | 6 mos. | | | | | | — |
| | 9 mos. | | | | | | — |
| | 12 mos. | | | | | | — |
| 53 | 1 | 397 | 438 | 396 | 4.5 | 6 | — |
| | 7 | 484 | 553 | 477 | 7 | 8.5 | 66.5 |
| | 14 | 580 | 529 | 528 | 9.5 | 9.5 | — |
| | 30 | 627 | 564 | 556 | 10 | 9.5 | — |
| | 60 | 670 | 677 | 582 | 10.5 | 10 | — |
| | 90 | 686 | 571 | 601 | 10 | 9.5 | — |
| | 6 mos. | | | | | | — |
| | 9 mos. | | | | | | — |
| | 12 mos. | | | | | | — |
| 54 | 1 | 213 | 211 | 208 | 2.5 | 2.5 | — |
| | 7 | 223 | 270 | 222 | 2.5 | 3.5 | 67.5 |
| | 14 | 265 | 235 | 236 | 4 | 3 | — |
| | 30 | 285 | 241 | 244 | 4 | 3 | — |
| | 60 | 294 | 300 | 249 | 4 | 3.5 | — |
| | 90 | 298 | 230 | 245 | 4 | 3 | — |
| | 6 mos. | | | | | | — |
| | 9 mos. | | | | | | — |
| | 12 mos. | | | | | | — |

Example 49: Evaluation of PCC1 FAS in Toothpaste

The data for this series are found in Table 14.

The toothpaste produced from this suspension initially was soupy and lacking structure. This is a desired property for filling toothpaste tubes. The initial low viscosity allows manufacturers to fill tubes faster without any air pockets in the toothpaste tubes. The structure development of the paste occurred shortly after packout and is reflected in the viscosity, Cuban Value, and String Value data. A delayed structure (in one to 7 days) is also very much desired. The Cuban Value is an index of ribbon strength and stand-up on the brush and has a maximum value of 12. The Cuban Test is similar to the time test described in the U.S. Pat. No. 5,858,343 which is incorporated herein by reference. However, the two side panels had 13 total wires. The test was run in duplicate and numbers of toothpaste loops remained suspended after 15 seconds were called "Cuban values". The higher the number, the higher the ribbon strength and standing.

The string value is a measure of toothpaste stringiness, the lower the value the less stringy the paste. The string value was measured using the Voland-Stevens-LFRA Texture Analyzes using the following setting:

Distance=25 mm
Speed=2.0 mm/sec
Platform at maximum height*
Switch set to Normal
Push power Supply button on

*Platform should be adjusted so that the maximum height corresponds to a distance of exactly 13.0 cm between the top surface of the platform and the base of the LRFA case. This was accomplished by securing the platform stand with a clamp, in place of the pin supplied with the unit.

Overall, this suspension produced an acceptable toothpaste.

Toothpaste viscosity was measured at 25° C. using Brookfield Viscometer RVT, Model DV II with Helipath attachment. Spindle E was used at 5 rpm. A toothpaste sample kept in 4 ounce jar was used for the viscosity measurements. Total of six readings were taken over 3-minute time period. Readings were taken every 30 seconds and an average of six is reported.

Example 50: Evaluation of PCC1 FAS in Toothpaste

The glycerin free toothpaste produced from this suspension initially was soupy and lacking structure. Again, viscosity and structure development was observed shortly after packout and is reflected in the data. Overall, this system produced acceptable toothpaste.

Example 51: Evaluation of PCC2 (Dry) in Toothpaste (Control)

The toothpaste produced from the dry abrasive was very viscous at packout. Viscosity and structure development continued throughout the course of the study. Extremely high viscosities were observed for this material although Cuban Values remained relatively low. It would appear that the PCC2 also acts as a thickener within this system. Overall, this system produced unacceptable toothpaste due to high viscosity.

Example 52: Evaluation of PCC2 FAS in Toothpaste

The glycerin free toothpaste produced from this suspension was relatively viscous at packout and demonstrated little viscosity build during the course of the study. Structure development was observed in terms of increasing Cuban Values and overall this system produced acceptable toothpaste.

It was surprisingly found that the toothpaste made with the slurry (Example 52) had more stable viscosity compared to the dry addition of PCC2. That is it, during 90 days storage toothpaste made with FAS went from 486000 cps after one day to only 582,000 cps after 90 days. In contrast toothpaste made with dry PCC2 went from 754,000 cps after one day to 1,537,000 cps after 90 days. Such a rise in toothpaste viscosity with time is not preferred by the toothpaste manufacturers.

Example 53: Evaluation of Dical/Sylodent FAS in Toothpaste

The toothpaste produced from this system was moderately viscous at packout. This system demonstrated viscosity and structure build throughout the course of the study, which is reflected in the data. Overall, this system produced an acceptable toothpaste.

Example 54: Evaluation of Dical FAS in Toothpaste

The toothpaste produced from this system was very soupy and lacking structure at packout. Very little viscosity or structure development was observed at this Xanthan concentration, which is reflected in the data.

All samples remained stable and no settling or syneresis was observed. Overall, this system produced acceptable toothpaste.

In summary, by suspending the toothpaste abrasives, dusting can be minimized, and the overall toothpaste process time potentially can be reduced.

While the invention has been described with respect to specific embodiments, it should be understood that they are not intended to be limiting and that many variations and modifications are possible without departing from the scope and spirit of this invention.

What is claimed is:

1. A stable fluid abrasive suspension (FAS) composition consisting essentially of
    a) an abrasive selected from the group consisting of calcium carbonate ($CaCO_3$), precipitated calcium carbonate, calcium phosphate ($Ca_3(PO_4)_2$), sodium meta phosphate, calcium pryo-phosphate, dicalcium phosphate, sodium bicarbonate ($NaHCO_3$), silica, and alumina, wherein the amount of the abrasive has a lower limit of about 30 wt % based on the total weight of the composition,
    b) suspending vehicle selected from the group consisting of water, a polyhydric alcohol, and mixtures thereof, and the polyhydric alcohol is selected from the group consisting of sorbitol, glycerol, propylene glycol, polyethylene glycol, ribitol, xylitol, mannitol, and mixtures thereof, and
    c) a water-swellable or water-soluble polymer for stabilizing the FAS is a polysaccharide selected from the group consisting of carrageenan, carboxymethylcellulose (CMC), hydroxyethylcellulose (HEC), hydroxypropylcellulose (HPC), methylcellulose (MC), hydrorxypropylmethylcellulose (HPMC), ethylhydroxyethylcellulose (EHEC), carboxymethylhydroxyethylcellulose (CMHEC), xanthan gum, pectin, and mixtures thereof.

2. The fluid abrasive suspension composition of claim 1, wherein the amount of the abrasive has an upper limit of about 70 wt % based on the total weight of the composition.

3. The fluid abrasive suspension composition of claim 1, wherein the amount of the abrasive has an upper limit of about 60 wt % based on the total weight of the composition.

4. The fluid abrasive suspension composition of claim 1, wherein the amount of the abrasive has an upper limit of about 45 wt % based on the total weight of the composition.

5. The fluid abrasive suspension composition of claim 1, wherein the bulk density of the abrasive has a lower limit of about 0.2 g/ml.

6. The fluid abrasive suspension composition of claim 1, wherein the bulk density of the abrasive has a lower limit of about 0.4 g/ml.

7. The fluid abrasive suspension composition of claim 1, wherein the bulk density of the abrasive has a lower limit of its about 0.6 g/ml.

8. The fluid abrasive suspension composition of claim 1, wherein the bulk density of the abrasive has an upper limit of about 1.2 g/ml.

9. The fluid abrasive suspension composition of claim 1, wherein the bulk density of the abrasive has an upper limit of about 1.0 g/ml.

10. The fluid abrasive suspension composition of claim 1, wherein the bulk density of the abrasive has an upper limit of about 0.8 g/ml.

11. The FAS composition of claim 1, wherein water-soluble or water-swellable polymer is selected from the group consisting polysaccharide, inorganic gel forming or thickening agent, homo- or copolymer of acrylic acid or acrylic acid salt, polyvinylpyrolidene, gelatin and mixture thereof.

12. The fluid abrasive suspension composition of claim 11, wherein the amount of the polymer has a lower limit of about 0.1 wt % of the composition.

13. The fluid abrasive suspension composition of claim 11, wherein the amount of the polymer has a lower limit of about 0.5 wt % of the composition.

14. The fluid abrasive suspension composition of claim 11, wherein the amount of the polymer has a lower limit of about 1.0 wt % of the composition.

15. The fluid abrasive suspension composition of claim 11, wherein the amount of the polymer has an upper limit of about 10.0 wt % of the composition.

16. The fluid abrasive suspension composition of claim 11, wherein the amount of the polymer has an upper limit of about 7.0 wt % of the composition.

17. The fluid abrasive suspension composition of claim 11, wherein the amount of the polymer has an upper limit of about 3.0 wt % of the composition.

18. The fluid abrasive suspension composition of claim 1, wherein the amount of the suspending vehicle has a lower limit of 25 wt % based on the total composition.

19. The fluid abrasive suspension composition of claim 1, wherein the amount of the suspending vehicle has a lower limit of 30-wt % based on the total composition.

20. The fluid abrasive suspension composition of claim 1, wherein the amount of the suspending vehicle has a lower limit of 45-wt % based on the total composition.

21. The fluid abrasive suspension composition of claim 1, wherein the amount of the suspending vehicle has an upper limit of 90-wt % based on the total composition.

22. The fluid abrasive suspension composition of claim 1, wherein the amount of the suspending vehicle has an upper limit of 75-wt % based on the total composition.

23. The fluid abrasive suspension composition of claim 1, wherein the amount of the suspending vehicle has an upper limit of 60-wt % based on the total composition.

24. The fluid abrasive suspension of claim 1 of CaCO3, water, sorbitol and CMC or carrageenan.

25. The fluid abrasive suspension of claim 1, wherein the fluid polymer suspension is stable for at least 1 hours.

* * * * *